United States Patent
Makino et al.

(10) Patent No.: US 6,342,609 B2
(45) Date of Patent: *Jan. 29, 2002

(54) PROCESS FOR PREPARING 3-(7-AMIDINO-2-NAPHTHYL)-2-PHENYLPROPIONIC ACID DERIVATIVES

(75) Inventors: Toru Makino; Yukio Yokoyama, both of Tokyo (JP)

(73) Assignee: Daiichi Pharmaceutical Co., Ltd., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/424,227

(22) PCT Filed: May 29, 1998

(86) PCT No.: PCT/JP98/02379

§ 371 Date: Nov. 26, 1999

§ 102(e) Date: Nov. 26, 1999

(87) PCT Pub. No.: WO98/54132

PCT Pub. Date: Dec. 3, 1998

(30) Foreign Application Priority Data

May 30, 1997 (JP) ............................................. 9-142042

(51) Int. Cl.[7] ...................... C07D 207/04; C07D 207/12
(52) U.S. Cl. ........................ 548/541; 548/556; 548/557; 548/569
(58) Field of Search ................. 548/541, 556, 548/557, 569

(56) References Cited

FOREIGN PATENT DOCUMENTS

| JP | 5-208946 A | * | 8/1993 |
| JP | 6-227971 A | * | 8/1994 |
| WO | WO 96/02497 A1 | * | 8/1993 |

OTHER PUBLICATIONS

T. Nagahara, et al., "Dibasic (Amidinoaryl) Propanoic Acid Derivatives As Novel Blood Coagulation Factor Xa Inhibitors", *Journal of Medicinal Chemistry*, 1994, vol. 37, No. 8, pp. 1200–1207.

B. D. Judkins, et al., "A Versatile Synthesis Of Amidines From Nitriles Via Amidoximes", *Synthetic Communications*, 1996, vol. 26, No. 23, pp. 4351–4367.

H. Jendralla, et al., "Efficient Kg–Scale Synthesis Of Thrombin Inhibitor CRC 220", *Tetrahedron*, 1995, vol. 51, No. 44, pp. 12047–12068.

* cited by examiner

Primary Examiner—Floyd D. Higel
(74) Attorney, Agent, or Firm—Oblon, Spivak, McClelland, Maier & Neustadt, P.C.

(57) ABSTRACT

A process for industrially preparing intermediates of aromatic amidine derivatives having anticoagulant activity, i.e., compounds represented by formula (3) or salts thereof, by the following reaction scheme including (1), (2), and (3), wherein $R^1$ represents H or an alkyl group; and $R^3$ represents H, an alkyl group, or an alkanoyl group

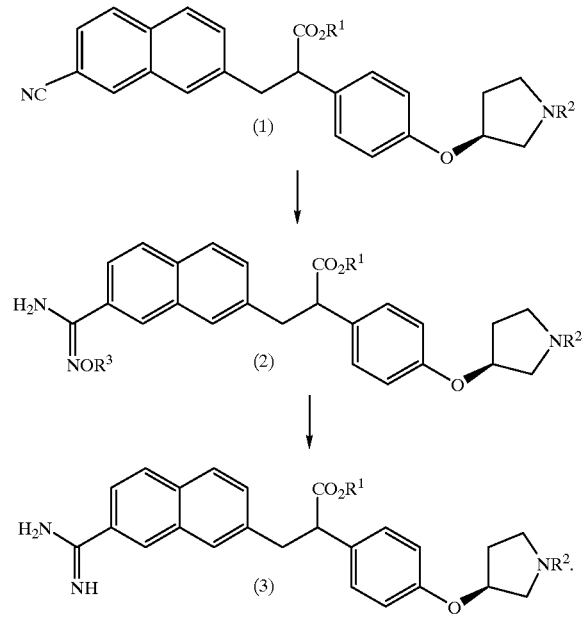

26 Claims, No Drawings

PROCESS FOR PREPARING 3-(7-AMIDINO-2-NAPHTHYL)-2-PHENYLPROPIONIC ACID DERIVATIVES

This application is a 371 of PCT/JP98/02379 filed May 29, 1998.

TECHNICAL FIELD

The present invention relates to an intermediate for preparing aromatic amidine derivatives having excellent anticoagulant activity based on inhibition of activated blood coagulation factor X (Japanese Patent Application Laid-Open (kokai) No. 5-208946), and to a process for preparing the intermediate.

BACKGROUND ART

Japanese Patent Application Laid-Open (kokai) No. 5-208946 discloses, as intermediates for preparing an aromatic amidine derivative, a compound represented by formula (3):

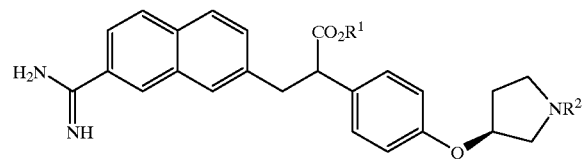

(3)

wherein $R^1$ represents a hydrogen atom or an alkyl group; and $R^2$ represents a hydrogen atom, an alkyl group, a formyl group, an alkanoyl group, a carbamoyl group, a monoalkylcarbamoyl group, a dialkylcarbamoyl group, a formimidoyl group, an alkanoimidoyl group, a benzimidoyl group, a carboxyl group, an alkoxycarbonyl group, a carboxyalkyl group, an alkylcarbonylalkyl group, an aminoalkyl group, an alkanoylamino group, an alkanoylaminoalkyl group, an aralkyl group, or an aralkyloxycarbonyl group;

and salts thereof. This publication also discloses a process for preparing the compound and salts.

The process comprises the following steps:

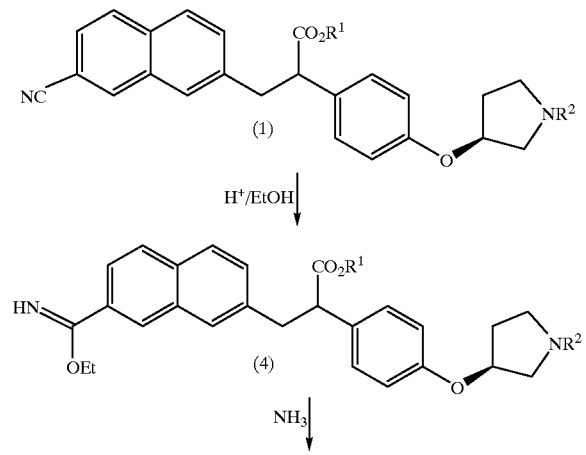

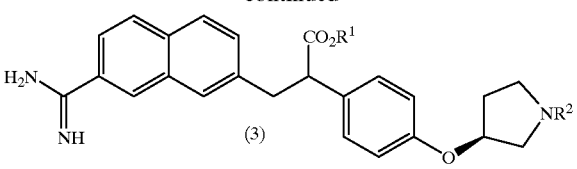

(3)

wherein $R^1$ and $R^2$ have the same definitions as described above and Et represents an ethyl group. That is, the process comprises reacting a compound represented by formula (1) (hereinafter referred to as nitrile compound (1)) or a salt thereof with ethanol in the presence of an acid; and reacting the thus-formed compound represented by formula (4) or a salt thereof with ammonia, to thereby form a compound represented by formula (3) (hereinafter referred to as amidine compound (3)) or a salt thereof.

However, in the process, when $R^2$ is a substituent cleaved by an acid (e.g., an alkoxycarbonyl group such as a tert-butoxycarbonyl), a by-product is formed. In addition, epimerization partially proceeds to thereby lower the optical purity of amidine compound (3). In order to suppress epimerization, reaction temperature must be maintained low, which requires a period of one week or more for synthesis of amidine compound (3) from nitrile compound (1) or a salt thereof. Moreover, the process is not suitable for large-scale production, in that a large amount of hydrogen chloride gas and ammonia gas must be used.

DISCLOSURE OF THE INVENTION

In view of the foregoing, the present inventors have conducted earnest studies, and have found an industrially advantageous process for preparing amidine compound (3) or salts thereof, which process permits production of the compound on a large scale at high yield and with a short reaction time without lowering the optical purity of the target compound.

The process according to the present invention is expressed by the following reaction scheme I or II:

Reaction Scheme I

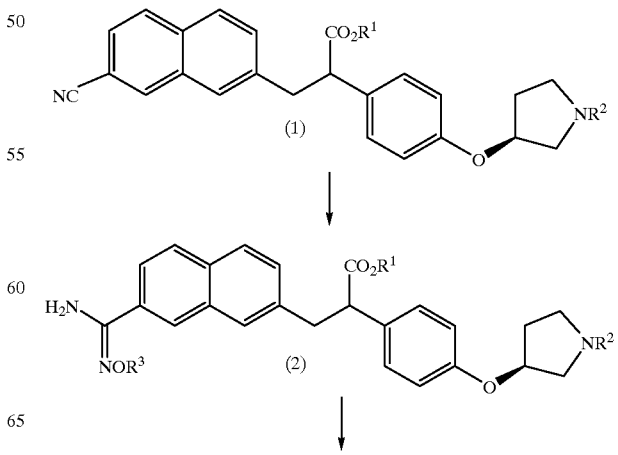

-continued

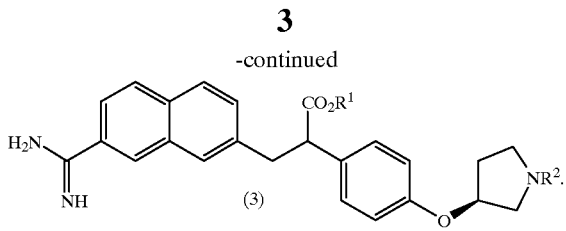

Reaction Scheme II:

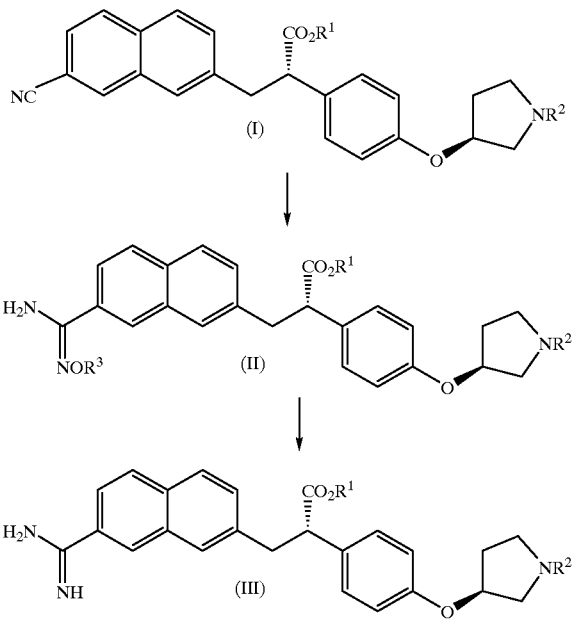

wherein $R^3$ represents a hydrogen atom, an alkyl group, or an alkanoyl group; and $R^1$ and $R^2$ have the same definitions as described above.

Accordingly, the present invention is directed to a process for producing amidine compound (3) or a salt thereof—or a compound represented by formula (III) (hereinafter referred to as amidine compound (III)) or a salt thereof—which process comprises reacting nitrile compound (1) or a salt thereof—or a compound represented by formula (I) (hereinafter referred to as nitrile compound (I)) or a salt thereof—with a hydroxylamine compound; and reducing the thus-formed compound represented by formula (2) (hereinafter referred to as amidoxime compound (2)) or a salt thereof, or the thus-formed compound represented by formula (II) (hereinafter referred to as amidoxime compound (II)) or a salt thereof.

The present invention is also directed to amidoxime compound (2) or salts thereof—or amidoxime compound (II) or salts thereof—the compounds and salts being useful intermediates in the process according to the present invention.

BEST MODE FOR CARRYING OUT THE INVENTION

The present invention will next be described in detail. First, substituents of the compounds of the present invention will be described.

$R^1$ represents a hydrogen atom or an alkyl group. Examples of the alkyl group include linear, branched, or cyclic C1–C6 alkyl groups. Specific examples include a methyl group, an ethyl group, a propyl group, an isopropyl group, a butyl group, an isobutyl group, a tert-butyl group, a pentyl group, a hexyl group, a cyclopropyl group, a cyclobutyl group, a cyclopentyl group, and a cyclohexyl group. Of these, an alkyl group is preferred, with a methyl group or an ethyl group being more preferred as $R^1$.

$R^2$ represents a hydrogen atom, an alkyl group, a formyl group, an alkanoyl group, a carbamoyl group, a monoalkylcarbamoyl group, a dialkylcarbamoyl group, a formimidoyl group, an alkanoimidoyl group, a benzimidoyl group, a carboxyl group, an alkoxycarbonyl group, a carboxyalkyl group, an alkylcarbonylalkyl group, an aminoalkyl group, an alkanoylamino group, an alkanoylaminoalkyl group, an aralkyl group, an aralkyloxycarbonyl group, or an alkanoyl group.

When $R^2$ is an alkyl group, examples thereof include the same alkyl groups as described in relation to $R^1$. Examples of the alkanoyl group include a group formed of a linear, branched, or cyclic C1–C6 alkyl group and a carbonyl group. Specific examples include an acetyl group and a propionyl group.

Examples of the monoalkylcarbamoyl group include a carbamoyl group in which one hydrogen atom is substituted with a linear, branched, or cyclic C1–C6 alkyl group. Specific examples include a monomethylcarbamoyl group, a monoethylcarbamoyl group, and a monoisopropylcarbamoyl group.

Examples of the dialkylcarbamoyl group include a carbamoyl group in which two hydrogen atoms are substituted with linear, branched, or cyclic C1–C6 alkyl groups, which may be identical to or different from each other. Specific examples include a dimethylcarbamoyl group, a diethylcarbamoyl group, and an ethylmethylcarbamoyl group.

The alkanoimidoyl group is a group formed of an alkyl group and a —C(=NH)— group. Examples include a —C(=NH)—$C_{1-6}$ alkyl group such as an acetimidoyl group.

Examples of the alkoxycarbonyl group include a group formed of a linear, branched, or cyclic C1–C6 alkoxyl group and a carbonyl group. Specific examples include a methoxycarbonyl group, an ethoxycarbonyl group, and a tert-butoxycarbonyl group.

Examples of the carboxyalkyl group include a group formed of a carboxyl group and a linear, branched, or cyclic C1–C6 alkylene group. Specific examples include a carboxymethyl group and a carboxyethyl group.

Examples of the alkylcarbonylalkyl group include a group formed of a linear, branched, or cyclic C1–C6 alkyl group, a carbonyl group, and a linear, branched, or cyclic C1–C6 alkylene group. Specific examples include a methylcarbonylmethyl group, a methylcarbonylethyl group, and a ethylcarbonylmethyl group.

Examples of the aminoalkyl group include a group formed of an amino group and a linear, branched, or cyclic C1–C6 alkylene group. Specific examples include an aminomethyl group, an aminoethyl group, and an aminopropyl group.

Examples of the alkanoylamino group include a group formed of the above-described alkanoyl group and an imino group. Specific examples include a formylamino group, an acetylamino group, and a propionylamino group.

Examples of the alkanoylaminoalkyl group include a group formed of the above-described alkanoylamino group and a linear, branched, or cyclic C1–C6 alkylene group. Specific examples include a formylaminomethyl group, an acetylaminomethyl group, a propionylaminoethyl group.

Examples of the aralkyl group include a group formed of an aryl group such as a phenyl group or a naphthyl group and a linear, branched, or cyclic C1–C6 alkylene group. Specific examples include a benzyl group, a phenethyl group, a triphenylmethyl group, and a naphthylmethyl group.

Examples of the aralkyloxycarbonyl group include a group formed of the above-described aralkyl group and an oxycarbonyl group. Specific examples include a benzyloxycarbonyl group and a p-nitrobenzyloxycarbonyl group.

In the present invention, examples of preferred $R^2$ include a hydrogen atom, an alkanoyl group, an alkoxycarbonyl group, an alkanoimidoyl group, an aralkyl group, or an aralkyloxycarbonyl group. Of these, a hydrogen atom, an acetyl group, a tert-butoxycarbonyl group, an acetimidoyl group, a benzyl group, and a benzyloxycarbonyl group are more preferred.

$R^3$ represents a hydrogen atom, an alkyl group, or an alkanoyl group. When $R^3$ is an alkyl group or an alkanoyl group, example alkyl groups and example alkanoyl groups are the same as described in relation to $R^1$. In the present invention, $R^3$ is preferably a hydrogen atom.

The process according to the present invention will next be described.

(Step A) Process for preparing amidoxime compound (2) or a salt thereof or amidoxime compound (II) or a salt thereof Amidoxime compound (2) or a salt thereof or amidoxime compound (II) or a salt thereof can be prepared through reaction of a hydroxylamine compound with nitrile compound (1) or a salt thereof or nitrile compound (I) or a salt thereof, wherein nitrile compound (1) or a salt thereof or nitrile compound (I) or a salt thereof is prepared through a method described, for example, in Japanese Patent Application Laid-Open (kokai) No. 5-208946.

Examples of the hydroxylamine compound include hydroxylamine or a salt thereof and an O-alkylhydroxylamine or a salt thereof such as O-methylhydroxylamine or O-ethylhydroxylamine. Such hydroxylamines may be represented by formula $NH_2OR^3$, wherein $R^3$ has the same definition as described above. These hydroxylamines may be used as such; e.g., in the form of liquid, solid, or gas, in the reaction. When the hydroxylamine compound is liquid, the compound may be used as a mixture with an appropriate solvent, whereas when the compound is solid, it may be used as a solution which is prepared by dissolving the compound in an appropriate solvent.

Examples of preferred hydroxylamine compounds in the present invention include hydroxylamine and a salt thereof. Specific examples include hydroxylamine, hydroxylammonium chloride, and hydroxylammonium sulfate. When they are used in the reaction, an aqueous solution of hydroxylamine, hydroxylammonium chloride and/or hydroxylammonium sulfate dissolved in an aqueous solution of sodium hydroxide is preferable.

Reaction of a hydroxylamine compound with nitrile compound (1) or a salt thereof or nitrile compound (I) or a salt thereof is preferably carried out in a solvent.

Examples of the solvent include C1–C6 alcohols such as methanol, ethanol, propanol, and butanol; ethers such as tetrahydrofuran and diisopropyl ether; aprotic polar solvents such as dimethylformamide and dimethyl sulfoxide; ketones such as acetone; and water. These solvents may be used singly or in combination of two or more species.

In the present invention, the solvent is preferably a C1–C6 alcohol or a solvent mixture containing a C1–C6 alcohol, more preferably ethanol or a solvent mixture containing ethanol.

The solvent is used in an amount of 2–50 ml based on 1 g of nitrile compound (1) or a salt thereof or nitrile compound (I) or a salt thereof, preferably 5–15 ml. The reaction is carried out in the temperature range of 0° C. to the boiling point of an employed solvent for 0.1–48 hours. Preferably, the reaction mixture is refluxed for 1–6 hours.

The thus-formed amidoxime compound (2) or amidoxime compound (II) can be isolated through crystallization, which is carried out by cooling the reaction mixture. Alternatively, amidoxime compound (2) or amidoxime compound (II) may also be crystallized from the reaction mixture as a salt. Examples of the salt include mineral acid salts such as hydrochloride and sulfate, and organic sulfonates such as methanesulfonate and p-toluenesulfonate.

The reaction mixture may optionally be subjected to extraction with a solvent such as ethyl acetate, chloroform, dichloromethane, dichloroethane, toluene, or butanol. The resultant extract containing amidoxime compound (2) or amidoxime compound (II) may be used as is in the subsequent step.

(Step B) Process for preparing amidine compound (3) or a salt thereof or amidine compound (III) or a salt thereof Amidine compound (3) or a salt thereof may be prepared through reduction of amidoxime compound (2) or a salt thereof, and amidine compound (III) or a salt thereof may be prepared through reduction of amidoxime compound (II) or a salt thereof. Specifically, amidoxime compound (2) or a salt thereof or amidoxime compound (II) or a salt thereof may be reduced by 1) hydrogenation by use of a metallic catalyst, or 2) reduction in the presence of a metal such as zinc, iron, or titanium.

Examples of metallic catalysts used in hydrogenation include nickel catalysts, palladium catalysts, platinum catalysts, and rhodium catalysts. A nickel catalyst refers to a nickel compound and a nickel compound carried by carbon, barium sulfate, or diatomaceous earth. The same applies to the case of other metallic catalysts such as palladium, platinum, and rhodium catalysts.

In the process, a palladium catalyst is preferably used. Examples of palladium catalysts include palladium black, palladium-barium sulfate with barium sulfate serving as a carrier, and palladium-carbon. Of these, palladium-carbon is preferably used.

The amount of a metallic catalyst used in the process may be appropriately determined, and, for example, 0.001–0.5 g of 10% palladium-carbon may be used with respect to 1 g of amidoxime compound (2) or a salt thereof or amidoxime compound (II) or a salt thereof.

For hydrogenation by use of a metallic catalyst, examples of a hydrogen source include hydrogen gas, isopropanol, silane, formic acid, and a formic acid salt. Of these, formic acid is preferably used. The hydrogen source may be used in an amount of 1 equivalent or more, and, for example, when the hydrogen source is formic acid, formic acid may be used in an amount of 2–10 equivalents.

Hydrogenation is preferably performed in a solvent. Examples of the solvent include chloroform; dichloromethane; dichloroethane; toluene; C1–C6 alcohols such as methanol, ethanol, propanol, isopropanol, and butanol; ethers such as diethyl ether, diisopropyl ether, and tetrahydrofuran; esters such as ethyl acetate and ethyl formate; N,N-dimethylformamide; dimethylsulfoxide; and water. These solvents may be used singly or in combination of two or more species. In the process, C1–C6 alcohols and esters are preferably used, and, of these, ethanol or ethyl acetate is particularly preferred.

The amount of a solvent used in the reaction is 2–25 ml based on 1 g of amidoxime compound (2) or a salt thereof or amidoxime compound (II) or a salt thereof, preferably 2–15 ml. The reaction temperature is between 0° C. and the boiling point of a used solvent, preferably between 5 and 30° C. The reaction time is 0.1–24 hours, preferably 0.5–5 hours.

Reduction in the presence of a metal such as zinc, iron, or titanium is performed in the presence of an acid such as hydrochloric acid or sulfuric acid, or a salt such as ammonium hydrochloride, and the metal is used in an amount of 1 equivalent or more. Reduction in the presence of a metal is preferably performed in a solvent. Examples of the solvent include C1–C6 alcohols such as methanol, ethanol, propanol, isopropanol, and butanol; N,N-dimethylformamide; dimethylsulfoxide; and water. These solvents may be used singly or in combination of two or more species. In the process, C1–C6 alcohols are preferably used, and of these, methanol or ethanol is particularly preferred.

The amount of the solvent is 2–50 ml based on 1 g of amidoxime compound (2) or a salt thereof or amidoxime compound (II) or a salt thereof, preferably 5–15 ml. The reduction temperature is between 0° C. and the boiling point of the employed solvent, preferably at the reflux temperature. The reduction time is 0.1–24 hours, preferably 2–8 hours. When reduction is performed in the presence of a metal, a proton source is preferably used. Examples of the proton source include mineral acids such as hydrochloric acid, sulfuric acid, and nitric acid; salts of the mineral acids; organic acids such as formic acid and acetic acid; and salts of the organic acids. Of these, hydrochloric acid salts such as ammonium hydrochloride are preferably used.

In accordance with needs, the reaction mixture after reduction may be extracted by use of solvents for extraction such as ethyl acetate, chloroform, dichloromethane, dichloroethane, toluene, and butanol, and subsequently washed with water to thereby remove an unnecessary acid and salt, and the thus-treated reaction mixture may be used in the next step.

Amidine compound (3) or amidine compound (III) may be purified by crystallization as a salt thereof from the reaction mixture or the above-treated reaction mixture. Examples of salts of amidine compound (3) or amidine compound (III) include mineral acid salts such as hydrochlorides, hydrobromides, hydroiodides, tetrafluoroboronates, perchlorates, nitrates, and sulfates; organic sulfonates such as methanesulfonates, 2-hydroxyethanesulfonates, p-toluenesulfonates, and benzenesulfonates; and carboxylic acid salts such as formates, acetates, propionates, butyrates, pivalonates, oxalates, malonates, succinates, glutarates, adipates, tartrates, maleates, malates, mandelates, and benzoates. Of these, methanesulfonates, acetates, fumarates, maleates, succinates, mandelates, and benzoates are preferably used, and particularly maleates are preferably used.

When $R^3$ refers to a hydrogen atom, reduction of amidoxime compound (2) or amidoxime compound (II) may be performed after o-acylation by use of an acylating agent. After o-acylation, reduction may be easily performed, which is preferable. In this case, previously-acylated amidoxime compound (2) or amidoxime compound (II) may be reduced, or these compounds may be reduced in the presence of an acylating agent. Preferably, reduction is performed in the presence of an acylating agent, in consideration of convenience.

Examples of acylating agents include acid anhydrides such as acetic anhydride, benzoic anhydride, maleic anhydride, and phthalic anhydride; mixed acid anhydrides prepared from different carboxylic acids or from carboxylic acids and acid anhydrides; and acid chlorides such as benzoyl chloride and acetyl chloride. Specific examples of mixed acid anhydrides include a mixture prepared from formic acid and acetic anhydride. In the process, an acid anhydride and a mixed acid anhydride are preferably used as an acylating agent.

The amount of acylating agent used in acylation is 1 equivalent or more with respect to amidoxime compound (2) or amidoxime compound (II). In the process, acetic anhydride or a mixed acid anhydride prepared from formic acid and acetic anhydride is preferably used, and the amount of the acylating agent is equivalent to that of the amidoxime compound (2) or amidoxime compound (II).

In order to convert the substituent ($R^2$) on the nitrogen atom of the pyrrolidinyl group of amidine compound (3) or a salt thereof or amidine compound (III) or a salt thereof into a hydrogen atom, deprotection may be performed on amidine compound ((3) or (III)) or a salt thereof, wherein $R^2$ is a protective group of the nitrogen atom of the pyrrolidine ring, including alkoxycarbonyl groups such as a tert-butoxycarbonyl group; aralkyl groups such as a benzyl group; aralkyloxycarbonyl groups such as a benzyloxycarbonyl group; and alkanoyl groups such as an acetyl group. Specifically, deprotection may be performed by use of known reactions and methods, such as a method described in "Protective Groups in Organic Synthesis. 2nd Edition" by T. W. Green and P. G. M. Wuts. For example, in the case of an alkoxycarbonyl group, deprotection proceeds easily by reaction with an acid. Examples of employed acids include Inorganic acids such as hydrochloric acid and sulfuric acid, and organic acids such as methanesulfonic acid and p-toluenesulfonic acid. The acid may be used in an equiamount or more, or in great excess with respect to amidine compound ((3) or (III)). The reaction is preferably carried out in a solvent, and examples of employed solvents include ethanol, ethyl acetate, toluene, and N,N-dimethylformamide. These solvents may be used singly or in combination of two or more species. The reaction temperature is between −10° C. and the boiling temperature of an employed solvent, and the reaction time is between five minutes and 10 hours.

For example, when hydrochloric acid is used as an acid in deprotection, 1–10 ml of an ethanol solution containing 30 wt. % hydrochloric acid is used with respect to 1 g of amidine compound (3) or a salt thereof or amidine compound (III) or a salt thereof. In this case, deprotection may be performed at room temperature or less for five minutes to two hours. When sulfuric acid, methanesulfonic acid, or p-toluenesulfonic acid is used as an acid in deprotection, the acid is used in an amount of 1–5 equivalents and deprotection may be performed in ethanol for 1–5 hours with refluxing.

A compound corresponding to amidine compound (3) wherein the substituent ($R^2$) on the nitrogen atom of the pyrrolidinyl group is a hydrogen atom is represented by the following formula (3'):

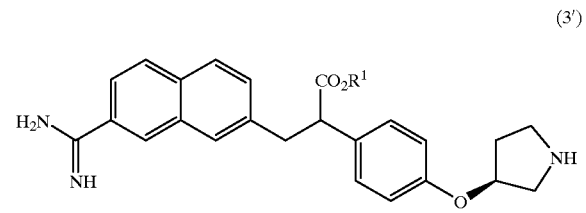

(3')

wherein $R^1$ is the same as described above.

A compound corresponding to amidine compound (III) wherein the substituent (R²) on the nitrogen atom of the pyrrolidinyl group is a hydrogen atom is represented by the following formula (III'):

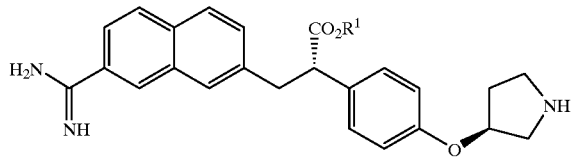

(III')

wherein R¹ is the same as described above.

After reaction or concentration, the compound prepared through the above-described reaction may be purified by isolation as a salt of the compound. Examples of the salts include mineral acid salts such as hydrochlorides, hydrobromides, hydroiodides, tetrafluoroboronates, perchlorates, nitrates, and sulfates; organic sulfonates such as methanesulfonates, 2-hydroxyethanesulfonates, p-toluenesulfonates, and benzenesulfonates; and carboxylic acid salts such as formates, acetates, propionates, butyrates, pivalonates, oxalates, malonates, succinates, glutarates, adipates, tartrates, maleates, malates, mandelates, and benzoates.

In the process, a compound and/or a salt of the compound comprises a solvate of the compound and a solvate of the salt of the compound. Examples of solvents include water and C1–C6 alcohols.

The thus-obtained amidine compound ((3') or (III')) or a salt thereof is reacted with alkyl acetimidate or a salt thereof, to thereby produce alkyl 2-[4-[[(3S)-1-acetimidoyl-3-pyrrolidinyl]oxy]phenyl]-3-(7-amidino-2-naphthyl) propionate (an acetimidoyl compound), which is a compound wherein the nitrogen atom on the pyrrolidine ring or the acetimidoyl group of amidine compound ((3') or (III')) is substituted, or to thereby produce a salt of the compound. In addition, the thus-produced acetimidoyl compound or a salt thereof is hydrolyzed to thereby prepare 2-[4-[[(3S)-1-acetimidoyl-3-pyrrolidinyl]oxy]phenyl]-3-(7-amidino-2-naphthyl)propionic acid or a salt thereof. In this case, acetimidoylation is performed, for example, by reaction between amidine compound (3') or a salt thereof and alkyl acetimidate or a salt thereof in an appropriate solvent in the presence of a base such as triethylamine, sodium hydroxide, or potassium hydroxide. The thus-prepared acetimidoyl compound or a salt thereof is hydrolyzed in the presence of a mineral acid such as hydrochloric acid or sulfuric acid or an organic acid such as p-toluenesulfonic acid at −20° C. to the reflux temperature. The aforementioned acetimidoylation and hydrolysis are described in Japanese Patent Application Laid-Open (kokai) No. 5-208946.

EXAMPLE 1

Ethyl (2S)-3-[7-amino(hydroxyimino)methyl-2-naphthyl]-2-[4-[[(3S)-1-tert-butoxycarbonyl-3-pyrrolidinyl]oxy]phenyl]propionate Hydroxylammonium sulfate (32.83 g) was dissolved in a 5N aqueous solution of sodium hydroxide (76 ml) at room temperature. The solution was added to ethanol (520 ml) with stirring. Ethyl (2S)-2-[4-[[(3S)-1-tert-butoxycarbonyl-3-pyrrolidinyl]oxy]phenyl]-3-(7-cyano-2-naphtyl) propionate (51.46 g) was suspended in the resultant solution at room temperature, followed by refluxing for 2 hours with stirring under heat. After completion of reaction was confirmed through TLC (chloroform:acetone=3:1), the resultant mixture was left to cool, and a precipitated inorganic salt was removed through filtration. The filtrate was subjected to crystallization at room temperature overnight with stirring. Water (520 ml) was added to the thus-formed suspension and the resultant mixture was further stirred for 3 hours at room temperature. The formed crystals were collected through filtration with suction. After being air-dried for one day, the crystals were dried at 50° C. under reduced pressure-for 8 hours, to thereby yield 53.14 g of the target compound (colorless crystals).

¹H-NMR (DMSO-d₆, ref. TMS=0.00 ppm) δ: 1.00 (3H, t, J=7 Hz), 1.38 (9H, d, J=5 Hz), 1.9~2.2 (2H, m), 3.1~3.6 (6H, m), 3.9~4.1 (3H, m), 4.95 (1H, m), 5.91 (2H, br) 6.89 (2H, d, J=8 Hz), 7.29 (2H, d, J=8 Hz), 7.39 (1H, d, J=9 Hz), 7.67 (1H, s), 7.7~7.9 (3H, m), 8.09 (1H, s), 9.76 (1H, br). FAB-MS: 548 (M+1), 532.

EXAMPLE 2

Ethyl (2S)-3-(7-amidino-2-naphtyl)-2-[4-[[(3S)-1-tert-butoxycarbonyl-3-pyrrolidinyl]oxy]phenyl]propionate maleic acid salt Ethyl (2S)-3-[7-amino(hydroxyimino)methyl-2-naphtyl]-2-[4-[[(3S)-1-tert-butoxycarbonyl-3-pyrrolidinyl]oxy]phenyl]propionate (5.476 g) and 10% palladium-carbon (0.548 g) were suspended in ethanol (50 ml). Acetic anhydride (0.95 ml) and formic acid (1.90 ml) were added to the suspension at room temperature with stirring. The resultant mixture was stirred at room temperature for 2 hours. After completion of reaction was confirmed, palladium-carbon was removed through filtration. After the filtrate was concentrated under reduced pressure, ethyl acetate (100 ml) and maleic acid (1.161 g) were added to the residue. The resultant mixture was heated at 85° C. for 10 minutes with stirring. After the mixture was cooled, precipitated crystals were collected through filtration. The crystals were dried at 50° C. under reduced pressure, to thereby yield 5.168 g of the target compound.

¹H-NMR (DMSO-d₆, ref. TMS=0.00 ppm) δ: 1.00 (3H, t, J=7 Hz), 1.39 (9H, d, J=6 Hz), 1.9~2.2 (2H, m), 3.1~3.6 (6H, m), 3.9~4.2 (3H, m), 4.95 (1H, m), 6.02 (2H, s), 6.89 (2H, d, J=9 Hz), 7.29 (2H, d, J=9 Hz), 7.62 (1H, dd, J=8, 1 Hz), 7.74 (1H, dd; J=8, 1 Hz), 7.85 (1 H, s), 7.96 (1H, d, J=8 Hz), 8.08 (1H, d, J=8 Hz), 8.34 (1H, s), 8.96, 9.40 (each 2H, br).

EXAMPLE 3

Ethyl (2S)-3-(7-amidino-2-naphtyl)-2-[4-[[(3S)-3-pyrrolidinyl]oxy]phenyl]propionate dihydrochloride Hydroxylammonium sulfate (1.64 g) was dissolved in a 5N aqueous solution of sodium hydroxide (3.8 ml) at room temperature. The resultant solution was added to ethanol (52 ml) with stirring. In the resultant mixture was suspended ethyl (2S)-2-[4-[[(3S)-1-tert-butoxycarbonyl-3-pyrrolidinyl]oxy]phenyl]-3-(7-cyano-2-naphtyl) propionate (5.15 g). The suspension was heated with stirring and refluxed for 4 hours. After completion of reaction was confirmed through TLC (chloroform:acetone=3:1), the resultant mixture was left to cool and concentrated under reduced pressure. The residue was dissolved by addition of ethyl acetate (50 ml) and water (50 ml). The ethyl acetate phase was separated and washed with water (50 ml), to thereby obtain a solution of ethyl (2S)-3-[7-amino (hydroxyimino)methyl-2-naphtyl]-2-[4-[[(3S)-1-tert-butoxycarbonyl-3-pyrrolidinyl]oxy]phenyl]propionate in ethyl acetate. 10% Palladium-carbon (0.548 g) was suspended in the solution. To the thus-formed suspension were added acetic anhydride (0.95 ml) and formic acid (1.90 ml) at 15° C. with stirring. After the mixture was stirred at 15° C. for 2 hours and completion of reaction was confirmed, 30% hydrogen chloride-ethanol (27 ml) was added and the resultant mixture was further subjected to stirring at 15° C. for 30 minutes. After completion of reaction was confirmed through HPLC, the solvent was concentrated to about half the amount under reduced pressure. Ethanol (27 ml) was added to the thus-concentrated solution and the resultant mixture was diluted, followed by filtration for removal of palladium-carbon. The filtrate was concentrated at reduced pressure. The residue was added to water (50 ml) and allowed to dissolve at room temperature. The thus-formed solution was purified though column chromatography employing a highly porous polymer type synthesized adsorbent (styrene-divinylbenzene polymer; DIAION HP-20) while a mixture of water and acetonitrile was used as a solvent. A small amount of diluted hydrochloric acid was added to the fraction containing the target compound. The resultant mixture was dried to solidify under reduced pressure to thereby obtain 4.62 g of the target compound. The thus-obtained ethyl (2S)-3-(7-amidino-2-naphtyl)-2-[4-[[(3S)-3-pyrrolidinyl]oxy]phenyl]propionate dihydrochloride was found to be identical to the compound obtained from synthesis described in Example 34 of Japanese Patent Application Laid-Open (kokai) No. 5-208946.

Reference Example 1

(2S)-2-[4-[[(3S)-1-acetimidoyl- 3-pyrrolidinyl]oxy]phenyl]-3-(7-amidino-2-naphtyl)propionic acid dihydrochloride.

((2S)-2-[4-[[(3S)-1-acetimidoyl-3-pyrrolidinyl]oxy]phenyl]-3-(7-amidino-2-naphtyl)propionis acid dihydrochloride (103.6 g) was obtained through the method described in Example 34, 40, or 46 of Japanese Patent Application Laid-Open (kokai) No. 5-208946, by use of ethyl (2S)-2-[4-[[(3S)-1-tert-butoxycarbonyl-3-pyrrolidinyl]oxy]phenyl]-3-(7-cyano-2-naphtyl)propionate (123.1 g, Optical purity: 99.7%). Optical purity of the thus-obtained compound was 94.8% de when measured under the HPLC conditions described in Example 46 of the specification of the above publication.

EXAMPLE 4

(2S)-2-[4-[[(3S)-1-acetimidoyl-3-pyrrolidinyl]oxy]phenyl]-3-(7-amidino-2-naphtyl)propionic acid dihydrochloride.

Ethyl (2S)-3-(7-amidino-2-naphtyl)-2-[4-[[(3S)-3-pyrrolidinyl]oxy]phenyl]propionate dihydrochloride (4.60 g) obtained from the synthesis described in Example 3 was used in the method described in Example 40 or 46 of Japanese Patent Application Laid-Open (kokai) No. 5-208946, to thereby obtain the target compound (4.35 g). Optical purity of the thus-obtained compound was 99.1% de when measured under the HPLC conditions described in Example 46 of the specification of the above publication. Further, through treatment similar to that described in Example 52 of the specification of the above publication, (2S)-2-[4-[[(3S)-1-acetimidoyl-3-pyrrolidinyl]oxy]phenyl]-3-(7-amidino-2-naphtyl)propionic acid hydrochloride pentahydrate was obtained.

INDUSTRIAL APPLICABILITY

Through a process disclosed in Japanese Patent Application Laid-Open (kokai) No. 5-208946; i.e.,

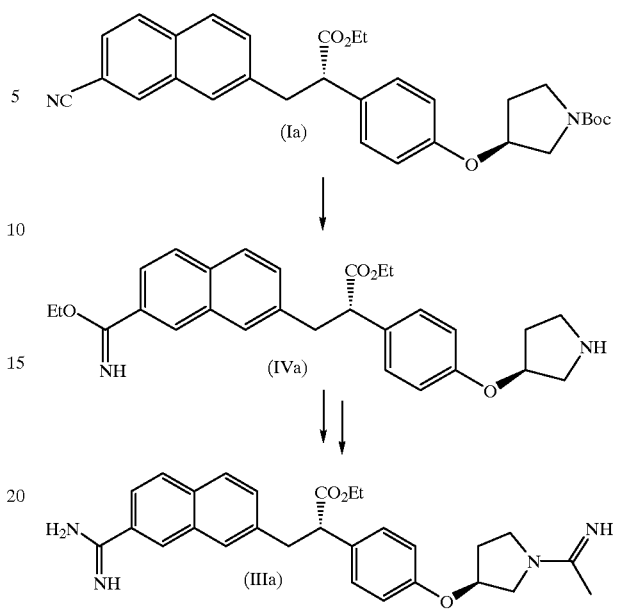

{wherein Et represents an ethyl group and Boc represents a tert-butoxycarbonyl group}, a (2S)-2-[4-[[(3S)-1-acetimidoyl-3-pyrrolidinyl]oxy]phenyl]-3-(7-amidino-2-naphthyl)propionic acid dihydrochloride represented by formula (IIIa) is derived from ethyl (2S)-2-[4-[[(3S)-1-tert-butoxycarbonyl-3-pyrrolidinyl]oxy]phenyl]-3-(7-cyano-2-naphthyl)propionate represented by (Ia) and having an optical purity of 99.7% de. In this case, the obtained compound (IIIa) has an optical purity of 94.8% de (see Reference Example 1).

In contrast, through a process according to the present invention; i.e.,

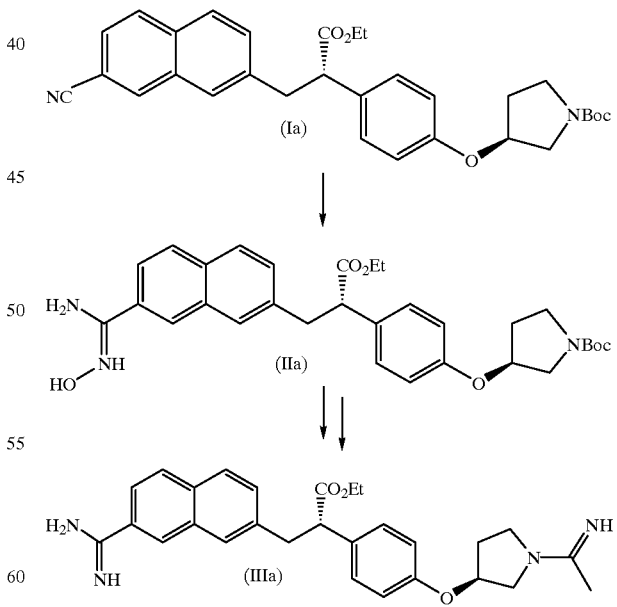

{wherein Et and Boc have the same definitions as described above}, compound (IIIa) is derived from compound (Ia) having an optical purity of 99.7% de. In this case, the obtained compound (IIIa) has an optical purity of 99.1% de and a high optical purity is maintained (see Example 4).

Briefly, substantial epimerization was not observed in the process according to the present invention.

The process according to the present invention is advantageous in that it can produce, on an industrial scale, intermediates for preparing aromatic amidine derivatives described in Japanese Patent Application Laid-Open (kokai) No. 5-208946 without lowering the optical purity.

We claim:

1. A process for producing a compound represented by formula (2) or a salt thereof:

(2)

[chemical structure]

wherein $R^1$ represents a hydrogen atom or an alkyl group; $R^2$ represents a hydrogen atom, an alkyl group, a formyl group, an alkanoyl group, a carbamoyl group, a monoalkylcarbamoyl group, a dialkylcarbamoyl group, a formimidoyl group, an alkanoimidoyl group, a benzimidoyl group, a carboxyl group, an alkoxycarbonyl group, a carboxyalkyl group, an alkylcarbonylalkyl group, an aminoalkyl group, an alkanoylamino group, an alkanoylaminoalkyl group, an aralkyl group, or an aralkyloxycarbonyl group; and $R^3$ represents a hydrogen atom, an alkyl group, or an alkanoyl group; which process comprises reacting a hydroxylamine compound with a compound represented by formula (1) or a salt thereof:

(1)

[chemical structure]

wherein $R^1$ and $R^2$ have the same meanings as defined above.

2. A process for producing a compound represented by formula (3) or a salt thereof:

(3)

[chemical structure]

wherein $R^1$ represents a hydrogen atom or an alkyl group; $R^2$ represents a hydrogen atom, an alkyl group, a formyl group, an alkanoyl group, a carbamoyl group, a monoalkylcarbamoyl group, a dialkylcarbamoyl group, a formimidoyl group, an alkanoimidoyl group, a benzimidoyl group, a carboxyl group, an alkoxycarbonyl group, a carboxyalkyl group, an alkylcarbonylalkyl group, an aminoalkyl group, an alkanoylamino group, an alkanoylaminoalkyl group, an aralkyl group, or an aralkyloxycarbonyl group;

which process comprises reducing a compound represented by formula (2) or a salt thereof:

(2)

[chemical structure]

wherein $R^1$ and $R^2$ have the same meanings as defined above and $R^3$ represents a hydrogen atom, an alkyl group, or an alkanoyl group.

3. A process for producing a compound represented by formula (3) or a salt thereof:

(3)

[chemical structure]

wherein $R^1$ represents a hydrogen atom or an alkyl group; $R^2$ represents a hydrogen atom, an alkyl group, a formyl group, an alkanoyl group, a carbamoyl group, a monoalkylcarbamoyl group a dialkylcarbamoyl group, a formimidoyl group, an alkanoimidoyl group, a benzimidoyl group, a carboxyl group, an alkoxycarbonyl group a carboxyalkyl group, an alkylcarbonylalkyl group, an aminoalkyl group, an alkanoylamino group, an alkanoylaminoalkyl group, an aralkyl group, or an aralkyloxycarbonyl group; which process comprises reacting a hydroxylamine compound represented formula (1) or a salt thereof:

(1)

[chemical structure]

wherein $R^1$ and $R^2$ have the same meanings as defined above; to thereby obtain a compound represented by formula (2) or a salt thereof:

(2)

[chemical structure]

wherein $R^1$ and $R^2$ have the same meanings as defined above and $R^3$ represents a hydrogen atom, an alkyl group or an alkanoyl group; and subsequently reducing the resultant compound represented by formula (2) or a salt thereof.

4. The process according to claim 1, wherein in formulas (1) and (2), $R^2$ is an alkanoyl group, an alkoxycarbonyl group, an aralkyl group, or an aralkyloxycarbonyl group.

5. The process according to claim 2, wherein in formulas (2) and (3), $R^2$ is an alkanoyl group, an alkoxycarbonyl group, an aralkyl group, or an aralkyloxycarbonyl group.

6. The process according to claim 3, wherein in formulas (1), (2), and (3), $R^2$ is an alkanoyl group, an alkoxycarbonyl group, an aralkyl group, or an aralkyloxycarbonyl group.

7. A process for producing 2-[4-[[(3S)-1-acetimidoyl-3-pyrrolidinyl]oxy]phenyl]-3-(7-amidino-2-naphthyl)propionic acid or a salt thereof, which comprises:

deprotecting a compound of formula (3) or a salt thereof obtained through the process as described in claim 5, wherein $R^2$ is an alkanoyl group, an alkoxycarbonyl group, an aralkyl group, or an aralkyloxycarbonyl group, to thereby yield an alkyl 3-(7-amidino-2-naphthyl)-2-[4-[[(3S)-3-pyrrolidinyl]oxy]phenyl]propionate or a salt thereof;

reacting the alkyl 3-(7-amidino-2-naphthyl)-2-[4-[[(3S)-3-pyrrolidinyl]oxy]phenyl]propionate or a salt thereof with alkyl acetimidate or a salt thereof, to thereby yield an alkyl 2-[4-[[(3S)-1-acetimidoyl-3-pyrrolidinyl]oxy]phenyl]-3-(7-amidino-2-naphthyl)propionate or a salt thereof; and then hydrolyzing the alkyl 2-[4-[((3S)-1-acetimidoyl-3-pyrrolidinyl]oxy]phenyl]-3-(7-amidino-2-naphthyl)propionate or a salt thereof.

8. A process for producing 2-[4-[[(3S)-1-acetimidoyl-3-pyrrolidinyl]oxy]phenyl]-3-(7-amidino-2-naphthyl)propionic acid or a salt thereof, which comprises:

deprotecting a compound of formula (3) or a salt thereof obtained through the process as described in claim 6, wherein $R^2$ is an alkanoyl group, an alkoxycarbonyl group, an aralkyl group, or an aralkyloxycarbonyl group, to thereby yield an alkyl 3-(7-amidino-2-naphthyl)-2-[4-[[(3S)-3-pyrrolidinyl]oxy]phenyl]propionate or a salt thereof;

reacting the alkyl 3-(7-amidino-2-naphthyl)-2-[4-[[(3S)-3-pyrrolidinyl]oxy]phenyl]propionate or a salt thereof with alkyl acetimidate or a salt thereof, to thereby yield an alkyl 2-[4-[[(3S)-1-acetimidoyl-3-pyrrolidinyl]oxy]phenyl]-3-(7-amidino-2-naphthyl)propionate or a salt thereof; and then hydrolyzing the alkyl 2-[4-[[(3S)-1-acetimidoyl-3-pyrrolidinyl]oxy]phenyl]-3-(7-amidino-2-naphthyl)propionate or a salt thereof.

9. A compound represented by formula (2) or a salt thereof:

(2)

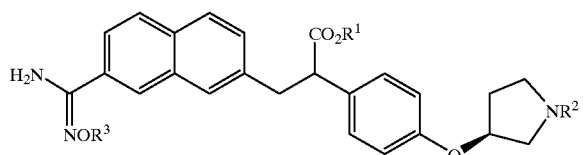

wherein $R^1$ represents a hydrogen atom or an alkyl group; $R^2$ represents a hydrogen atom, an alkyl group, a formyl group, an alkanoyl group, a carbamoyl group a monoalkylcarbamoyl group, a dialkylcarbamoyl group, a formimidoyl group, an alkanoimidoyl group, a benzimidoyl group, a carboxy group, an alkoxycarbonyl group, a carboxyalkyl group, an alkylcarbonylalkyl group, an aminoalkyl group, an alkanoylamino group, an alkanoylaminoalkyl group, an aralkyl group, or an aralkyloxycarbonyl group and $R^3$ represents a hydrogen atom, an alkyl group or an alkanoyl group.

10. Alkyl 3-[7-amino(hydroxyimino)methyl-2-naphthyl]-2-[4-[[(3S)-1-alkoxycarbonyl-3-pyrrolidinyl]oxy]phenyl]propionate or a salt thereof.

11. Alkyl 3-[7-amino(hydroxyimino)methyl-2-naphthyl]-2-[4-[[(3S)-1-tert-butoxycarbonyl-3-pyrrolidinyl]oxy]phenyl]-propionate or a salt thereof.

12. Alkyl 3-[7-amino(hydroxyimino)methyl-2-naphthyl]-2-[4-[[(3S)-3-pyrrolidinyl]oxy]phenyl]propionate or a salt thereof.

13. The process according to claim 1, wherein the compound represented by formula (1) is a compound of formula (I):

(I)

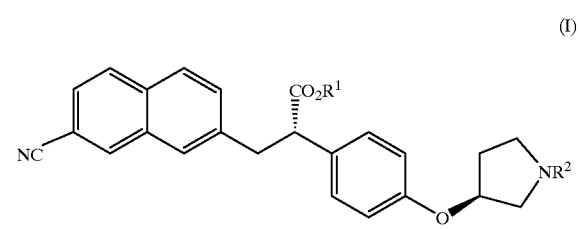

and the compound represented by formula (2) is a compound of formula (II):

(II)

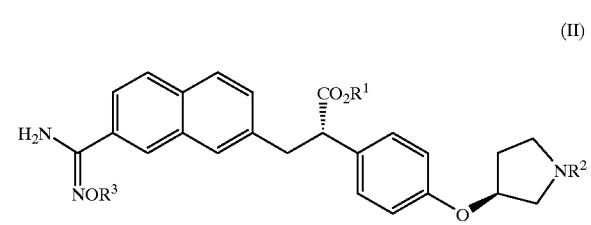

wherein $R^1$, $R^2$, and $R^3$ have the same meanings as defined above.

14. The process according to claim 2, wherein the compound represented by formula (2) is a compound of formula (II):

(II)

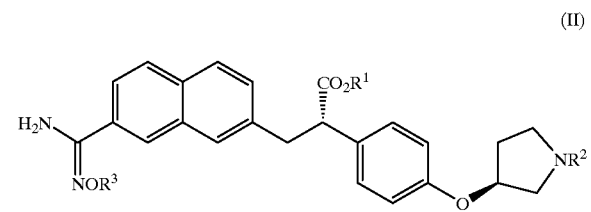

and the compound represented by formula (3) is a compound of formula (III):

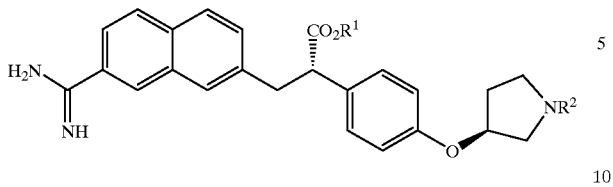

(III)

wherein R¹ and R² have the same meanings as defined above.

15. The process according to claim 3, wherein the compound represented by formula (1) is a compound of formula (I):

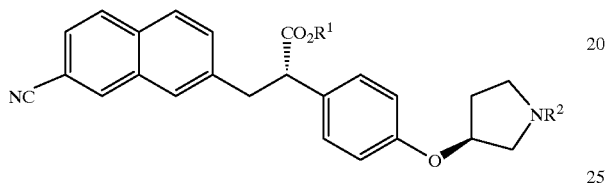

(I)

and the compound represented by formula (2) is a compound of formula (II):

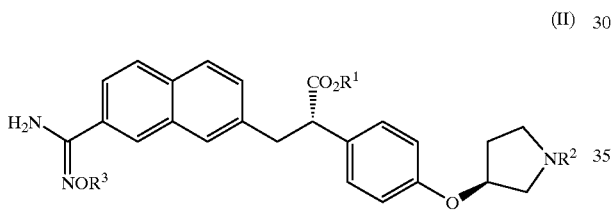

(II)

wherein R¹, R², and R³ have the same meanings as defined above, and the compound represented by formula (3) is a compound of formula (III):

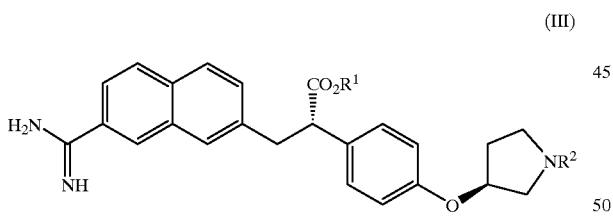

(III)

wherein R¹ and R² have the same meanings as defined above.

16. The process according to claim 13, wherein in formulas (I) and (II), R² is an alkanoyl group, an alkoxycarbonyl group, an aralkyl group, or an aralkyloxycarbonyl group.

17. The process according to claim 14, wherein in formulas (II) and (III), R² is an alkanoyl group, an alkoxycarbonyl group, an aralkyl group, or an aralkyloxycarbonyl group.

18. The process according to claim 15, wherein in formulas (I), (II), and (III), R² is an alkanoyl group, an alkoxycarbonyl group, an aralkyl group, or an aralkyloxycarbonyl group.

19. A process for producing (2S)-2-[4-[[(3S)-1-acetimidoyl-3-pyrrolidinyl]oxy]phenyl]-3-(7-amidino-2-naphthyl)propionic acid or a salt thereof, which comprises:

deprotecting a compound of formula (III) or a salt thereof obtained through the process as described in claim 17, wherein R² is an alkanoyl group, an alkoxycarbonyl group, an aralkyl group, or an aralkyloxycarbonyl group, to thereby yield an alkyl (2S)-3-(7-amidino-2-naphthyl)-2-[4-[[(3S)-3-pyrrolidinyl]oxy]phenyl]propionate or a salt thereof;

reacting the alkyl (2S)-3-(7-amidino-2-naphthyl)-2-[4-[[(3S)-3-pyrrolidinyl]oxy]phenyl]propionate or a salt thereof with alkyl acetimidate or a salt thereof, to thereby yield an alkyl (2S)-2-[4-[[(3S)-1-acetimidoyl-3-pyrrolidinyl]oxy]phenyl]-3-(7-amidino-2-naphthyl)propionate or a salt thereof; and then hydrolyzing the alkyl (2S)-2-[4-[[(3S)-1-acetimidoyl-3-pyrrolidinyl]oxy]phenyl]-3-(7-amidino-2-naphthyl)propionate or a salt thereof.

20. A process for producing (2S)-2-[4-[[(3S)-1-acetimidoyl-3-pyrrolidinyl]oxy]phenyl]-3-(7-amidino-2-naphthyl)propionic acid or a salt thereof, which comprises:

deprotecting a compound of formula (III) or a salt thereof obtained through the process as described in claim 18, wherein R² is an alkanoyl group, an alkoxycarbonyl group, an aralkyl group, or an aralkyloxycarbonyl group, to thereby yield an alkyl (2S)-3-(7-amidino-2-naphthyl)-2-[4-[[(3S)-3-pyrrolidinyl]oxy]phenyl]propionate or a salt thereof;

reacting the alkyl (2S)-3-(7-amidino-2-naphthyl)-2-[4-[[(3S)-3-pyrrolidinyl]oxy]phenyl]propionate or a salt thereof with alkyl acetimidate or a salt thereof, to thereby yield an alkyl (2S)-2-[4-[[(3S)-1-acetimidoyl-3-pyrrolidinyl]oxy]phenyl]-3-(7-amidino-2-naphthyl)propionate or a salt thereof; and then hydrolyzing the alkyl (2S)-2-[4-[[(3S)-1-acetimidoyl-3-pyrrolidinyl]oxy]phenyl]-3-(7-amidino-2-naphthyl)propionate or a salt thereof.

21. A compound represented for formula (II) or a salt thereof:

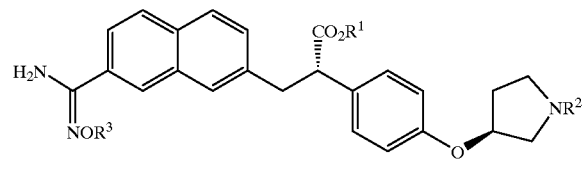

(II)

wherein R¹ represents a hydrogen atom or an alkyl group; R² represents a hydrogen atom, an alkyl group, a formyl group, an alkanoyl group, a carbamoyl group a monoalkylcarbamoyl group, a dialkylcarbamoyl group, a formimidoyl group, an alkanoimidoyl group, a benzimidoyl group, a carboxyl group, an alkoxycarbonyl group, a carboxyalkyl group, an alkylcarbonylalkyl group, an aminoalkyl group, an alkanoylamino group, an alkanoylaminoalkyl group an aralkyl group, or an aralkyloxycarbonyl group and R³ represents a hydrogen atom, an alkyl group, or an alkanoyl group.

22. Alkyl (2S)-3-[7-amino(hydroxyimino)methyl-2-naphthyl]-2-[4-[[(3S)-1-alkoxycarbonyl-3-pyrrolidinyl]oxy]phenyl]propionate or a salt thereof.

23. Alkyl (2S)-3-[7-amino(hydroxyimino)methyl-2-naphthyl]-2-[4-[[(3S)-1-tert-butoxycarbonyl-3-pyrrolidinyl]oxy]phenyl]propionate or a salt thereof.

24. Alkyl (2S)-3-[7-amino(hydroxyimino)methyl-2-naphthyl]-2-[4-[[(3S)-3-pyrrolidinyl]oxy]phenyl]propionate or a salt thereof.

25. The process according to claim 19, wherein the product obtained from said process is (2S)-2-[4[[(3S)-1-acetimidoyl-3-pyrrolidinyl]oxy]phenyl]-3-(7-amidino-2-naphthyl)propionic acid hydrochloride pentahydrate.

26. The process according to claim 20, wherein the product obtained from said process is (2S)-2-[4[[(3S)-1-acetimidoyl-3-pyrrolidinyl]oxy]phenyl]-3-(7-amidino-2-naphthyl)propionic acid hydrochloride pentahydrate.

* * * * *

UNITED STATES PATENT AND TRADEMARK OFFICE
CERTIFICATE OF CORRECTION

PATENT NO.    : 6,342,609 B2
DATED         : January 29, 2002
INVENTOR(S)   : Toru Makino et al.

It is certified that error appears in the above-identified patent and that said Letters Patent is hereby corrected as shown below:

Column 16,
Line 47, "as defined above" should read -- as defined in claim 1 --;

Column 17,
Line 11, "as defined above" should read -- as defined in claim 2 --;
Lines 39-40, "as defined above" should read -- as defined in claim 3 --;
Line 52, "as defined above" should read -- as defined in claim 3 --.

Signed and Sealed this

Third Day of December, 2002

JAMES E. ROGAN
*Director of the United States Patent and Trademark Office*